(12) United States Patent
Arata et al.

(10) Patent No.: US 7,359,115 B2
(45) Date of Patent: Apr. 15, 2008

(54) SAMPLE OBSERVATION METHOD, MICROSCOPE, AND SOLID IMMERSION LENS, OPTICAL CONTACT LIQUID USED IN THE METHOD

(75) Inventors: Ikuo Arata, Hamamatsu (JP); Shigeru Sakamoto, Hamamatsu (JP); Hirotoshi Terada, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 357 days.

(21) Appl. No.: 10/876,776

(22) Filed: Jun. 28, 2004

(65) Prior Publication Data

US 2005/0063046 A1  Mar. 24, 2005

(30) Foreign Application Priority Data

Oct. 31, 2003  (JP) .......................... P2003-373078

(51) Int. Cl.
*G02B 3/12*  (2006.01)
(52) U.S. Cl. ....................... 359/365; 359/368
(58) Field of Classification Search ...................... None
See application file for complete search history.

(56) References Cited

U.S. PATENT DOCUMENTS 5,220,403 A * 6/1993 Batchelder et al. ......... 356/450

6,594,086 B1   7/2003  Pakdaman et al. .......... 359/656
2002/0006558 A1 * 1/2002 Kobayashi et al. ............ 430/7

FOREIGN PATENT DOCUMENTS

| CN | 1279628 A | 1/2001 |
|---|---|---|
| JP | 05-157701 | 6/1993 |
| JP | 06-300824 | 10/1994 |
| JP | 07-190946 | 7/1995 |
| JP | 2002-236087 | 8/2002 |
| JP | 2003-207601 | 7/2003 |
| WO | WO 99/25487 | 5/1999 |
| WO | WO 03/062864 | 7/2003 |

* cited by examiner

Primary Examiner—Arnel Lavarias
Assistant Examiner—Derek S. Chapel
(74) Attorney, Agent, or Firm—Drinker Biddle & Reath LLP

(57) ABSTRACT

Optical contact liquid containing an amphipathic molecule is dripped onto a semiconductor device which is a sample as an inspection object (S104), and a solid immersion lens is set thereon (S105). The inserted position of the solid immersion lens is then adjusted (S106). The optical contact liquid is then dried (S108), and thereby the solid immersion lens is brought into optically-close contact with the semiconductor device. As a result, a sample observation method and a microscope or the like can be realized, in which the solid immersion lens can be easily aligned to a desired position on the sample, and the solid immersion lens can be securely brought into optically-close contact with the sample.

10 Claims, 12 Drawing Sheets

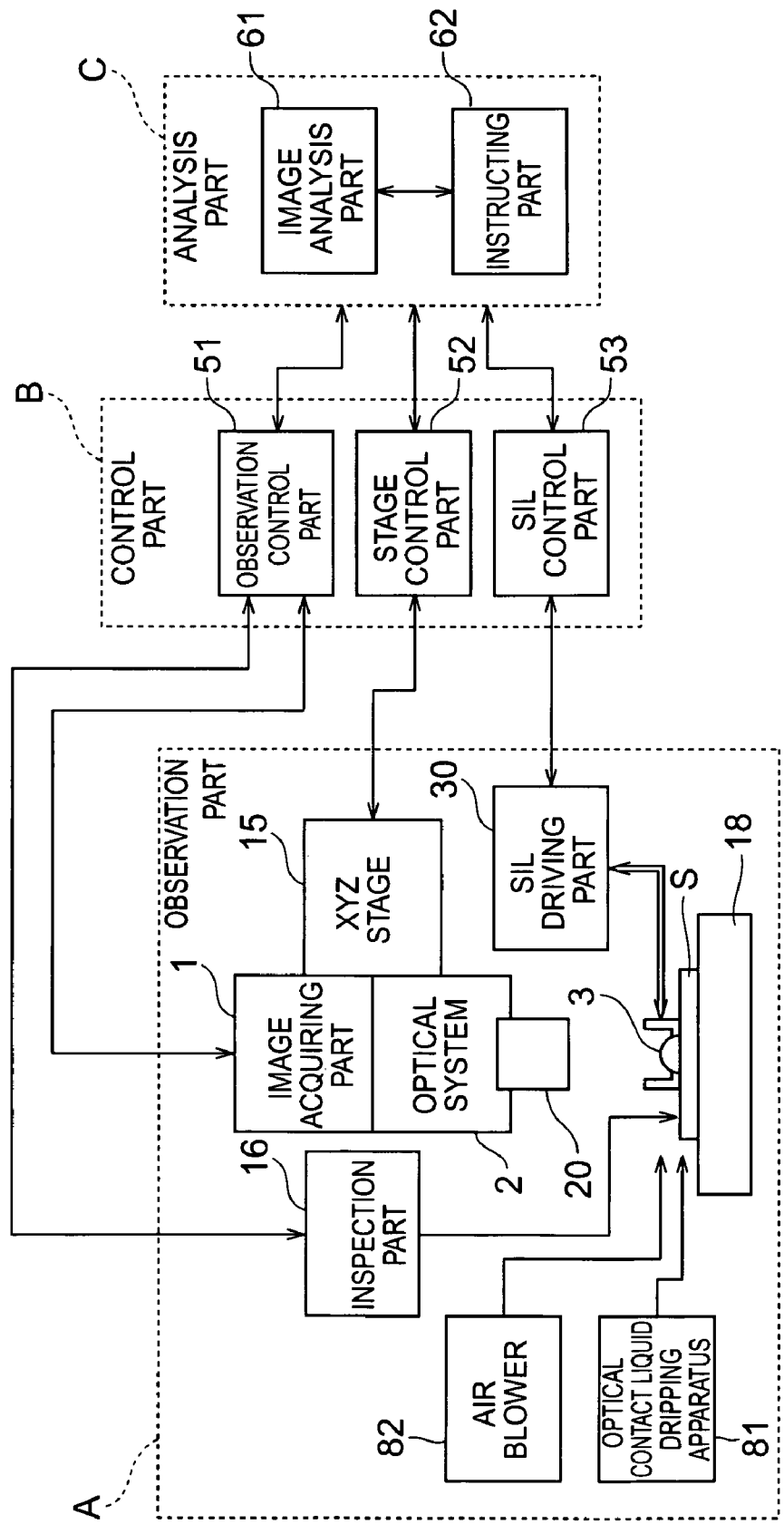

SAMPLE OBSERVATION METHOD, MICROSCOPE, AND SOLID IMMERSION LENS, OPTICAL CONTACT LIQUID USED IN THE METHOD

BACKGROUND OF THE INVENTION

1. Field of the Invention

The present invention relates to a sample observation method and a microscope used for observing a sample such as an electronic device, and a solid immersion lens used in the method and optical contact liquid for the solid immersion lens.

2. Related Background of the Invention

An electronic device as a sample is observed by a microscope or the like during inspection of the electronic device such as a semiconductor device, and a method for performing failure analysis and reliability evaluation of the electronic device is used. An emission microscope and an IR-OBIRCH apparatus or the like are conventionally known as an apparatus for inspecting a semiconductor (see Document 1: Japanese Patent Application Laid-Open No. H07-190946, and Document 2: Japanese Patent Application Laid-Open No. H06-300824). However, electronic devices which are inspection objects have been miniaturized in recent years, and the fine structure is difficult to analyze by a limitation caused by the diffraction limit of an optical system in a conventional inspection apparatus using visible light and infrared light.

Therefore, when the above fine structure of the electronic device is analyzed and the positions of an abnormality generated in the circuit patterns of transistors and wirings or the like formed in the electronic device are detected, the range where the abnormal positions exist is first narrowed down to some extent by an inspection apparatus using visible light, infrared light or heat rays. A method for inspecting the abnormal positions of the electronic device is used, in which the range narrowed down is observed by using an observation device such as an electronic microscope having high-resolution.

As described above, in the method for observing in high-resolution using the electronic microscope after inspection using light is performed, a problem exists in that much labor and time are required for inspecting the electronic device since the preparation and setting of the electronic device which is an inspection object are complex.

On the other hand, a solid immersion lens (SIL) is known as a lens for magnifying the image as the observation object. The solid immersion lens is a hemispherical lens or a hyperhemispherical lens which is called Weierstrass sphere. When the solid immersion lens is set so as to be brought into optically-close contact with the surface as the observation object, numerical aperture NA and magnification can be increased, and observation at higher spatial resolution is enabled. For instance, examples of electronic device inspection apparatuses using the above solid immersion lens are disclosed in Document 3: Japanese Patent Publication No. H7-18806, and Document 4: U.S. Pat. No. 6,594,086.

SUMMARY OF THE INVENTION

The solid immersion lens disclosed in Document 3 is a plano-convex lens, and the mounting surface for the observation object is a plane. At the time of observation, high refractive index fluid (index matching liquid) is interposed between the plano-convex lens and the observation object if necessary.

For instance, at the time of observing the semiconductor substrate as the observation object by using the solid immersion lens, when a gap is generated between the solid immersion lens and the semiconductor substrate which is the observation object, an incident light having an incident angle of a critical angle or more is totally reflected, and only a light having an incident angle of a critical angle or less is propagated. Thereby the effective numerical aperture is limited by the critical angle. However, when the gap between the solid immersion lens and the surface of the semiconductor substrate becomes the same degree as the wavelength of light in the semiconductor, the light can be propagated by evanescent coupling.

However, large gap parts may exist, resulting in a wide contact area in the gap between the plano-convex lens and the surface of the semiconductor substrate. The strength of a transmitted light lowers rapidly in the above large gap parts, and only a light having an incident angle of a critical angle or less can be propagated. Thereby, the effective numerical aperture is limited.

A method for obtaining the original resolution of the solid immersion lens without using the evanescent coupling is described in Document 3, in which the high refractive index fluid is interposed between the plano-convex lens and the observation object. Typical examples of high refractive index fluids include arsenic tripromide/disalmide/selenium compound system. However, since the arsenic tripromide has toxicity and corrosiveness, a handling problem exits.

The solid immersion lens disclosed in Document 4 is a bi-convex lens. Since the lens for which the mounting surface is brought into a point of contact with the observation object has a convex shape it is advantageous for securing contact. However, since the contact area with the observation object is very small, when the substrate of the semiconductor device which is the observation object becomes thick, light flux having high NA cannot pass in the substrate. In this case, a problem exits in that the original high resolution and high collecting efficiency of the solid immersion lens cannot be obtained.

It is necessary to apply pressure between the bottom of the solid immersion lens and the observation object so as to bring the solid immersion lens into close contact at a wide area with the observation object. In the rear surface analysis of the semiconductor device, it is necessary to adjust the pressure applied to the semiconductor substrate by sufficiently considering strength at the time of treating so as not to ruin the integrated circuits formed on the surface of the semiconductor substrate. In view of the tendency of thinning of the semiconductor device, the bi-convex lens cannot obtain the original resolution of the solid immersion lens.

Though distortion is generated in the semiconductor device by pressure, since this state is different from the mounting state of the semiconductor device, the demand for inspecting under the same operation conditions as the mounting state cannot be satisfied. In a state where distortion is generated, the result of contradicting the purpose of the original inspecting may arise.

It is an object of the present invention to provide a sample observation method and a microscope which can easily align a solid immersion lens to the desired position in a sample such as an electronic device which is an observation object and can bring the solid immersion lens into optically-close contact with the sample securely without applying excessive pressure, and to provide a solid immersion lens used in the method and optical contact liquid for the solid immersion lens.

In order to achieve the aforementioned object, a sample observation method of the present invention for observing a sample to obtain the internal information, comprises: a lens setting step of setting a solid immersion lens on a sample in a state where optical contact liquid containing an amphipathic molecule is interposed; a lens contacting step of closely contacting the solid immersion lens with the sample optically by evaporating the optical contact liquid; and an image acquiring step of acquiring the observation image of the sample magnified by the solid immersion lens through the solid immersion lens.

In the above sample observation method, when the solid immersion lens is brought into optically-close contact with the sample such as an electronic device, the optical contact liquid is interposed between the sample and the solid immersion lens, and the solid immersion lens is set on the sample. Herein, the optical contact liquid contains an amphipathic molecule. The amphipathic molecule contained in the optical contact liquid causes a decrease in the surface tension of the optical contact liquid, and thereby the wettability on the surface of the sample can be improved. Therefore, the optical contact liquid is spread on the surface of the sample, and the solid immersion lens can be easily positioned to the desired position.

Since the optical contact liquid contains the amphipathic molecule, the power keeping the wettability between the surface of the sample and the mounting surface of the solid immersion lens becomes dominant. Therefore, it is possible to bring the solid immersion lens into optically-close contact with the sample securely without applying excessive pressure in a process for drying the optical contact liquid. The present inventor found that as an additional effect physical fixing was obtained between the sample and the solid immersion lens in the state where the solid immersion lens was brought into optically-close contact with the sample by the optical contact liquid.

In the present invention, "optical close contact" means a state where the solid immersion lens is optically coupled to the sample through evanescent coupling. In the present invention, "internal information" shall, for example, in cases where electronic devices are to be the samples, include the circuit patterns of electronic devices as well as emission of weak light from electronic devices. Such weak light emissions include those caused by an abnormal position due to a defect in an electronic device, transient light emission that accompanies the switching operation of a transistor inside an electronic device, etc. The generation of heat due to a defect in an electronic device is also included.

The above sample observation method can be suitably used as a method for inspecting an electronic device. In this case, it is preferable that an electronic device inspection method for acquiring the image of an electronic device to detect the internal information, comprises: a lens setting step of setting a solid immersion lens on an electronic device in a state where optical contact liquid containing an amphipathic molecule is interposed; a lens contacting step of closely contacting the solid immersion lens with the electronic device optically by evaporating the optical contact liquid; and an image acquiring step of acquiring the observation image of the electronic device magnified by the solid immersion lens through the solid immersion lens.

In the above electronic device inspection method, when the solid immersion lens is brought into optically-close contact with the electronic device, the optical contact liquid is interposed between the electronic device and the solid immersion lens, and the solid immersion lens is set on the electronic device. Herein, the optical contact liquid contains an amphipathic molecule. The amphipathic molecule contained in the optical contact liquid causes a decrease in the surface tension of the optical contact liquid, and thereby the wettability on the substrate surface of the electronic device can be improved. Therefore, the optical contact liquid is spread on the substrate surface of the electronic device, and the solid immersion lens can be easily positioned to the desired position.

Since the optical contact liquid contains the amphipathic molecule, the power keeping the wettability between the substrate surface of the electronic device and the mounting surface of the solid immersion lens becomes dominant. Therefore, it is possible to bring the solid immersion lens into optically-close contact with the electronic device securely without applying excessive pressure in a process for drying the optical contact liquid. The present inventor found that physical fixing was obtained as an additional effect between the substrate of the electronic device and the solid immersion lens in the state where the solid immersion lens was brought into optically-close contact with the electronic device substrate by the optical contact liquid.

The sample observation method of the present invention for observing a sample to obtain the internal information, may comprise: a lens setting step of setting a solid immersion lens the mounting surface of which is treated with a hydrophilic treatment on a sample; a lens contacting step of closely contacting the solid immersion lens with the sample optically; and an image acquiring step of acquiring the observation image of the sample magnified by the solid immersion lens through the solid immersion lens.

In the above method for observing a sample, the solid immersion lens can be easily positioned to the desired position. Furthermore, it is possible to bring the solid immersion lens into optically-close contact with the sample securely without applying excessive pressure. In this case, it is preferable that in the lens setting step, a solid immersion lens the mounting surface of which is treated with a hydrophilic treatment is set on a sample in a state where the optical contact liquid is interposed, and in the lens contacting step, the optical contact liquid is evaporated to bring the solid immersion lens into optically-close contact with the sample.

The sample observation method of the present invention for observing a sample to obtain the internal information, may comprise: a lens setting step of setting a solid immersion lens on a sample the mounting surface of which is treated with a hydrophilic treatment; a lens contacting step of closely contacting the solid immersion lens with the sample optically; and an image acquiring step of acquiring the observation image of the sample magnified by the solid immersion lens through the solid immersion lens. In this case, it is preferable that the sample observation method further comprises a hydrophilic treatment step of treating the mounting surface of the sample with a hydrophilic treatment.

Herein, it is preferable that the sample observation method further comprises a separating step of wetting a position of the sample with which the solid immersion lens is brought into close contact by the optical contact liquid or the solvent of the optical contact liquid to separate the solid immersion lens from the sample after the image acquiring step. Thus, optical contact liquid or the solvent thereof is re-infiltrated to a boundary surface of the solid immersion lens and the sample by wetting the contact part by the optical contact liquid or the solvent thereof after the image acquiring step, and thereby the evanescent coupling can be released. In addition, because the physical fixing between the solid immersion lens and the sample can be released, it is possible to separate the solid immersion lens from the sample without damaging them, and thereby the solid immersion lens can be reused.

A surfactant molecule is preferably used as the amphipathic molecule of the optical contact liquid.

The solid immersion lens can be easily positioned by using the surfactant molecule as the amphipathic molecule. In addition, it is possible to bring the solid immersion lens into optically-close contact with the sample securely without applying excessive pressure. It is preferable to use an ionic surfactant molecule or a nonionic surfactant molecule as the surfactant molecule.

In the solid immersion lens of the present invention for observing a sample (for instance, analyzing the rear surface of the electronic device), the mounting surface is treated with a hydrophilic treatment.

Thus, if the solvent (for instance, water) of the optical contact liquid is used, the wettability of the mounting surface of the solid immersion lens can be improved in the same manner as the optical contact liquid which contains an amphipathic molecule by treating the mounting surface of the solid immersion lens with a hydrophilic treatment. As a result, the solid immersion lens can be easily positioned, and it is possible to bring the solid immersion lens into optically-close contact with the sample securely without applying excessive pressure. The physical fixing can be obtained between the sample and the solid immersion lens.

Herein, when the sample (for instance, the substrate of an electronic device) is a hydrophobe, the area containing at least the observation position on the sample is preferably treated with a hydrophilic treatment. It is preferable that the above hydrophilic treatment is performed by the physical adsorption, chemical adsorption or coating of a hydrophilic group.

The optical contact liquid (for instance, the optical contact liquid which is used for a semiconductor inspection method which acquires the image of an electronic device and detects the internal information) of the present invention used when a sample is observed, comprising an amphipathic molecule, whereby bringing the solid immersion lens into optically-close contact with the sample.

The wettability of the surface of the sample and mounting surface of the solid immersion lens can be improved by using above the optical contact liquid. As a result, the solid immersion lens can be easily positioned, and it is possible to bring the solid immersion lens into optically-close contact with the sample securely without applying excessive pressure. The physical fixing can be obtained between the sample and the solid immersion lens.

Herein, the amphipathic molecule may be a surfactant molecule. It is preferable to use an ionic surfactant molecule or a nonionic surfactant molecule as the surfactant molecule.

It is preferable that the optical contact liquid contains the surfactant molecule within the concentration range where the ratio of the surfactant molecule to the critical micelle concentration is more than 0 and no more than 400 times.

As a result of experiments described below, the optical coupling between the solid immersion lens and the sample is inferior to the above range in the range which deviates from the above range. Therefore, it is preferable that the optical contact liquid contains the surfactant molecule within the concentration range where the ratio of the surfactant molecule to the critical micelle concentration is 0 to 400 times. It is more preferable that the optical contact liquid is used, which contains the surfactant molecule within the concentration range where the ratio of the surfactant molecule to the critical micelle concentration is 1 to 100 times.

The microscope of the present invention for observing a sample to obtain the internal information, comprising: an optical system which contains an objective lens onto which the light from the sample is made incident and guides the image of the sample; a solid immersion lens for observing the sample; and an optical contact liquid dripping apparatus for dripping optical contact liquid containing an amphipathic molecule.

The sample can be observed in high resolution through the solid immersion lens according to the above construction. The solid immersion lens can be efficiently treated when applying to the sample observation by coupling the surface of the sample with the mounting surface of the solid immersion lens optically by using the optical contact liquid which contains the amphipathic molecule. Therefore, a microscope which can easily observe the fine structure of the sample can be achieved.

Herein, the microscope may be provided with an image acquiring means for acquiring the image of the sample which is to be an observation object. In this case, the optical system guides the image of the sample to the image acquiring means.

The above microscope can be suitably used as an electronic device inspection apparatus. In this case, it is preferable that the electronic device inspection apparatus for acquiring the image of an electronic device to inspect the internal information, comprising: an image acquiring means for acquiring the image of the electronic device which is an inspection object; an optical system which contains an objective lens onto which the light from the electronic device is made incident and guides the image of the electronic device to the image acquiring means; a solid immersion lens for analyzing the rear surface of the electronic device; and an optical contact liquid dripping apparatus for dripping optical contact liquid containing an amphipathic molecule.

The electronic device can be observed in high resolution through the solid immersion lens by the above electronic device inspection apparatus. The solid immersion lens can be efficiently treated when applying to the electronic device inspection by coupling the substrate surface of the electronic device with the mounting surface of the solid immersion lens optically by using the optical contact liquid which contains an amphipathic molecule. Therefore, an electronic device inspection apparatus which can easily inspect the electronic device such as analysis of the fine structure can be achieved.

It is preferable that the microscope having the above construction further comprises an air blower for drying the optical contact liquid. When this configuration is employed, the drying of the optical contact liquid can be quickened. At this time, the time required for bringing the solid immersion lens into optically-close contact with the surface of the sample can be remarkably reduced.

The microscope according to the present invention for observing a sample to obtain the internal information, may comprise: an optical system which contains an objective lens onto which the light from the sample is made incident and guides the image of the sample; and a solid immersion lens the mounting surface of which is treated with a hydrophilic treatment for observing the sample.

The sample can be observed at high resolution through the solid immersion lens by the microscope having the above construction. The solid immersion lens can be efficiently treated when applying to the sample observation. Therefore, a microscope which can easily observe the fine structure of the sample can be achieved. In this case, it is preferable that the microscope further comprises an optical contact liquid dripping apparatus for dripping optical contact liquid.

BRIEF DESCRIPTION OF THE DRAWINGS

FIG. 1 is a block diagram schematically showing a semiconductor inspection apparatus used for a semiconductor inspection method according to the embodiment of the present invention.

DESCRIPTION OF THE PREFERRED EMBODIMENTS

Figure 2A:
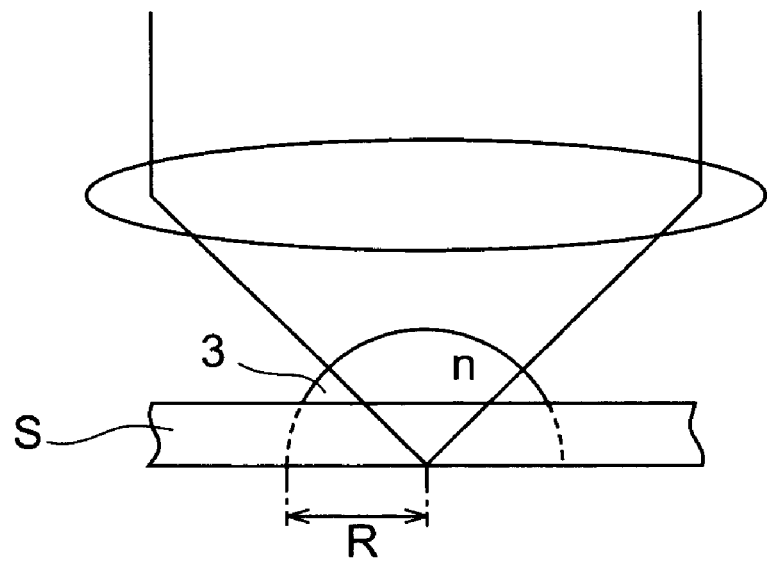
FIG. 2A and FIG. 2B are views showing the construction of a solid immersion lens and an example of an inspection method.

Hereinafter, the preferred embodiments of a sample observation method and a microscope, and a solid immersion lens and optical contact liquid used in the method according to the present invention will be described in detail with reference to the drawings. In each embodiment, identical components having the same function are designated by the same reference numerals, and overlapping description is omitted. The dimensional ratio of the drawings does not necessarily correspond to that of the description.

FIG. 1 is a block diagram schematically showing a semiconductor inspection apparatus (an electronic device inspection apparatus) used for a semiconductor inspection method (an electronic device inspection method) according to the embodiment of the present invention. In the semiconductor inspection apparatus used in the embodiment, for example, a semiconductor device S as an electronic device in which the circuit patterns which contain transistors and wirings or the like are formed on a semiconductor substrate is the sample of an inspection object (observation object), and the internal information is detected by acquiring the image of the semiconductor device S. Herein, the microscope, the sample observation method, the solid immersion lens and the optical contact liquid according to the invention can be applied when the sample is observed in general and the internal information is obtained. However, hereinafter, the application example to the semiconductor inspection will be mainly described.

The semiconductor inspection apparatus according to the embodiment is provided with an observation part A for observing a semiconductor device S, a control part B for controlling the operation of each part of the observation part A, and an analysis part C for performing the processing and instruction required for inspecting the semiconductor device S. The inspection object due to the semiconductor inspection apparatus according to the embodiment, that is, the semiconductor device S which is a sample as an observation object due to the microscope is placed on a stage 18 arranged in the observation part A.

The observation part A is provided with an image acquiring part 1 set in a dark box (not shown), an optical system 2, and a solid immersion lens (SIL) 3. The image acquiring part 1 contains a photodetector or an image pickup device or the like, and is a means for acquiring the image of the semiconductor device S. The optical system 2 which guides the image due to light from the semiconductor device S to the image acquiring part 1 is arranged between the image acquiring part 1 and the semiconductor device S placed on the stage 18.

An objective lens 20 onto which the light from semiconductor device S is made incident is arranged at a prescribed position opposite the semiconductor device S in the optical system 2. The light emitted or reflected from the semiconductor device S is made incident onto the objective lens 20, and reaches image acquiring part 1 through the optical system 2 containing the objective lens 20. The image of the semiconductor device S used for the inspection is acquired in the image acquiring part 1.

The image acquiring part 1 and the optical system 2 are composed integrally in a state where respective optical axes coincide with each other. An XYZ stage 15 is set for the image acquiring part 1 and the optical system 2. As a result, the image acquiring part 1 and the optical system 2 are moved if necessary in X and Y directions (a horizontal direction), and in a Z direction (a vertical direction), and thereby the image acquiring part 1 and the optical system 2 can be aligned and focused to the semiconductor device S.

An inspection part 16 is set for the semiconductor device S which is an inspection object. The inspection part 16 controls the state of the semiconductor device S if necessary when inspecting the semiconductor device S. Though a method for controlling the state of the semiconductor device S by the inspection part 16 is different depending on the specific inspection method applied to the semiconductor device S, for instance, a method for supplying the voltage to a prescribed part of circuit patterns formed on the semiconductor device S or a method for irradiating the semiconductor device S with a laser light as a probe light is used.

Figure 2B:
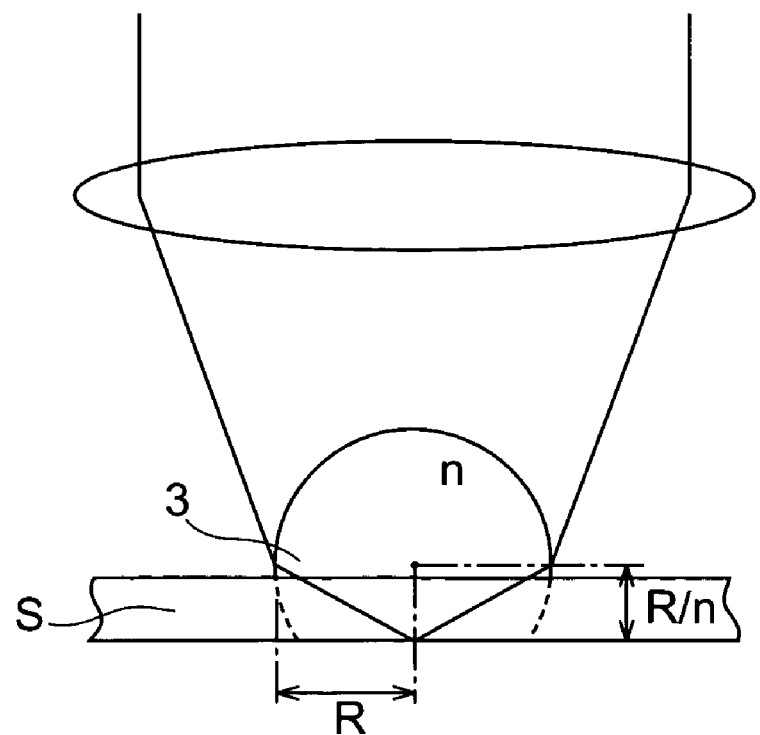

In the embodiment, a solid immersion lens 3 is set in the observation part A. FIG. 2A and FIG. 2B show the construction of a solid immersion lens and an example of the sample observation method using the same. The solid immersion lens 3 is generally a hemispherical lens or a hyperhemispherical lens which is called the Weierstrass sphere, and as shown in FIG. 2A and FIG. 2B, the solid immersion lens 3 is set so as to be brought into close contact with the substrate surface of the semiconductor device S which is the observation object.

When the minute optical element manufactured by a material having the refractive index which is similar to the refractive index of the semiconductor substrate is brought into optically-close contact with the substrate surface of the semiconductor device, the semiconductor substrate itself can be used as a part of the solid immersion lens. The analysis of the rear surface of the semiconductor device using the solid immersion lens can prevent the focus position from being deeper than in air atmosphere by the effect of the solid immersion lens when the focal point of the objective lens coincides with the integrated circuit formed on the surface of the semiconductor substrate. As a result, light flux having high NA can pass in the substrate, and high-resolution can be expected. Herein, the radius of solid immersion lens 3 is set to R, and the refractive index is set to n.

The lens shape of the above solid immersion lens 3 is determined by a condition where the aberration is eliminated. As shown in FIG. 2A, in the solid immersion lens having a hemispherical shape, the center of the sphere becomes a focus. At this time, the numerical aperture NA and the magnification become n times. On the other hand, as shown in FIG. 2B, in the solid immersion lens having a hyperhemispherical shape, a position shifting downward by only R/n from the center of the sphere becomes a focal point. At this time, the numerical aperture NA and the magnification become $n^2$ times. Or a position existing between the center of the sphere and a position shifting downward by only R/n from the center of the sphere may become a focal point. Thus, the solid immersion lens 3 may be used for conditions other than the conditions shown in FIG. 2A and FIG. 2B according to a specific observation condition or the like to the semiconductor device S.

It is preferable that a bottom part which is a mounting surface for the semiconductor device S has a toroidal shape in the solid immersion lens 3 according to the embodiment. The toroidal shape means a curved surface (toroidal surface) obtained from the curve defined in a Y-Z plane with a rotation axis of a straight line which passes the point of the distance of R from a starting point on a Z axis and is in parallel with a Y axis when a XYZ plane is defined. However, herein, a curved surface obtained from a straight line defined by the Y-Z plane with a rotation axis of a straight line being in parallel with the Y axis, that is, a cylindrical shape (cylindrical surface) is also contained in the toroidal shape (toroidal surface). Specifically, the solid immersion lens 3 is formed to the cylindrical shape in the embodiment.

When the solid immersion lens 3 is formed to the toroidal shape, the ratio of the curvature radius of the toroidal shape in the X direction to the curvature radius in the Y direction which is larger than the curvature radius in the X direction is preferably within the range of 1:1.5 to 1: ∞, and more preferably 1:3 to 1: ∞. When the curvature radius in the Y direction is less than 1.5 times of that in the X direction or is less than 3 times, the degree of close-contact at the time of bringing the solid immersion lens into optically-close contact with the observation object lowers. When the ratio of the curvature radius of the toroidal shape in the X direction to the curvature radius in the Y direction is 1: ∞, the toroidal shape becomes the cylindrical shape.

The solid immersion lens which can be applied to the present invention is not limited to the one having the above toroidal surface, and is also applied to the solid immersion lens having a plano-convex shape disclosed in Japanese Patent Publication No. H7-18806.

When the observation object is the semiconductor device, a material which is substantially equal to or near the refractive index of the substrate material and has a high refractive index is suitably used as the material of the solid immersion lens. The examples thereof include Si, GaP, and GaAs. In addition, when the observation object is an electronic device using a glass substrate or a plastic substrate, it is preferable to use glass or plastic as the material of the solid immersion lens.

The solid immersion lens 3 is movably set to the image acquiring part 1, the optical system 2 and the semiconductor device S placed on the stage 18 in the semiconductor device inspection apparatus shown in FIG. 1. Specifically, solid immersion lens 3 is composed so as to be moved between the inserted position containing an optical axis from semiconductor device S to the objective lens 20, at which the solid immersion lens 3 is brought into close contact with the surface of semiconductor device S as mentioned above, and the position (standby position) off the optical axis.

A solid immersion lens driving part 30 is arranged for the solid immersion lens 3. The solid immersion lens driving part 30 is a driving means for driving the solid immersion lens 3 to move the solid immersion lens 3 between the above-described inserted position and the standby position. In addition, the solid immersion lens driving part 30 adjusts the inserted position of the solid immersion lens 3 with respect to the objective lens 20 of the optical system 2 by moving the position of the solid immersion lens 3 minutely. FIG. 1 shows the solid immersion lens 3 set at the inserted position between the objective lens 20 and the semiconductor device S.

A control part B and an analysis part C are arranged for the observation part A which carries out observation, etc., for inspecting the semiconductor device S.

The control part B has an observation control part 51, a stage control part 52 and a solid immersion lens control part 53. The observation control part 51 controls the execution of the observation and the setting of the observation condition of the semiconductor device S performed in the observation part A by controlling the operation of the image acquiring part 1 and the inspection part 16.

The stage control part 52 controls the setting, alignment, focusing, etc., of the observation position of the semiconductor device S by the image acquiring part 1 and the optical system 2, as an inspection position (the observation position in the microscope) in the inspection apparatus by controlling the operation of the XYZ stage 15. The solid immersion lens control part 53 controls the movement of the solid immersion lens 3 between the inserted position and the standby position or the adjustment of the inserted position of the solid immersion lens 3 by controlling the operation of the solid immersion lens driving part 30.

The analysis part C has an image analysis part 61 and an instructing part 62. The image analysis part 61 performs the analysis or the like required for the image acquired by the image acquiring part 1. The instructing part 62 refers to the content of the input from an operator and the analysis content or the like by the image analysis part 61, and performs the instruction required for executing the inspection of the semiconductor device S in the observation part A through the control part B.

Particularly, in the embodiment, the analysis part C performs the processing and instruction required for the inspection of the semiconductor device S using the solid immersion lens with respect to the installation of the solid immersion lens 3 and the solid immersion lens driving part 30 set in the observation part A.

That is, when the solid immersion lens 3 is inserted between the objective lens 20 and the semiconductor device S, the image acquiring part 1 acquires the image containing a reflected light from the solid immersion lens 3 in the observation part A in a state where the solid immersion lens 3 is positioned at the inserted position. In the analysis part C, the image analysis part 61 performs a prescribed analysis, such as determining the position of the center of gravity of the image of the reflected light of the image containing the reflected light from the solid immersion lens 3 acquired by the image acquiring part 1. The instructing part 62 refers to the image containing the reflected light from the solid immersion lens 3 analyzed by the image analysis part 61, and instructs to adjust the position where the solid immersion lens 3 is inserted so that the position of the center of gravity of the image of the reflected light coincides with the inspection position in the semiconductor device S with respect to the solid immersion lens control part 53.

Figure 3:
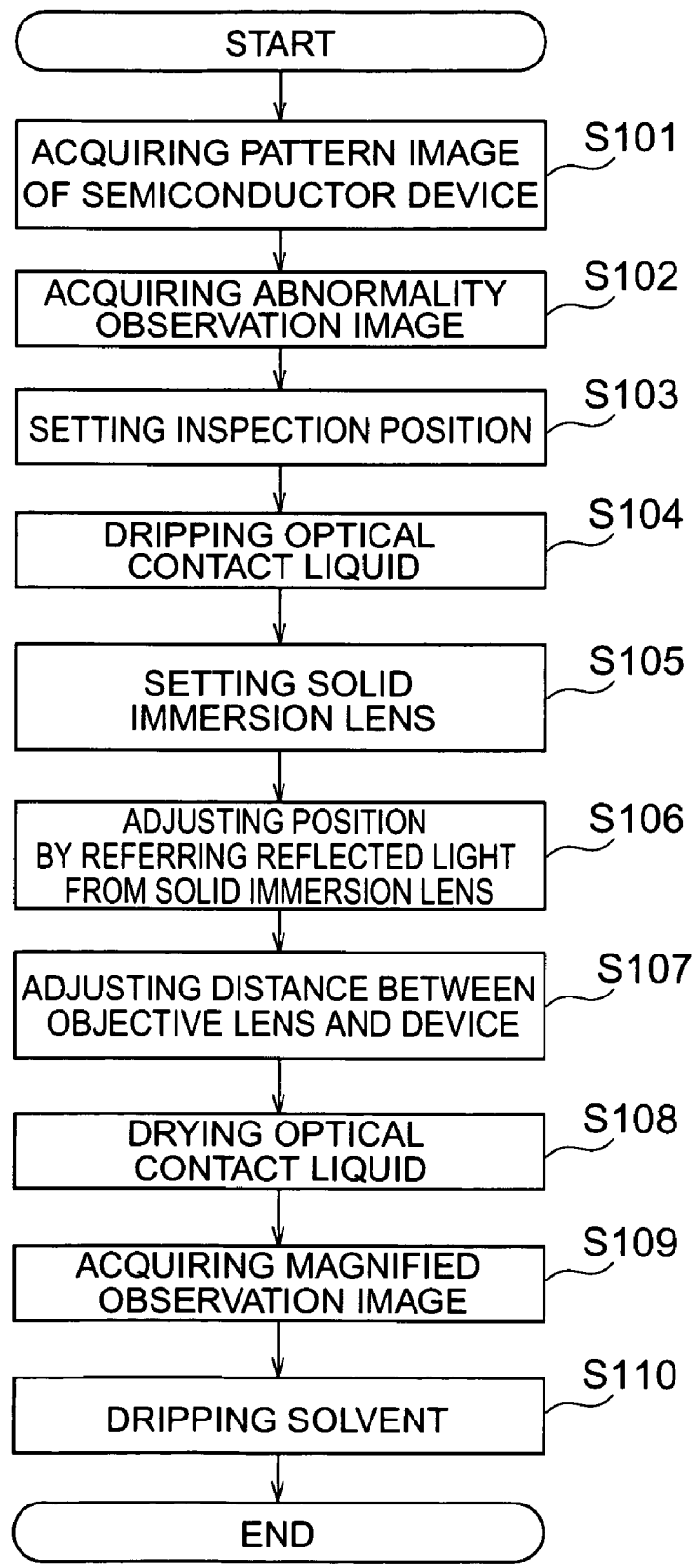
FIG. 3 is a flowchart showing the procedure of a semiconductor inspection method according to the embodiment.

Next, the semiconductor inspection method (sample observation method) according to the present invention using an semiconductor inspection apparatus (microscope) having the above construction will be described. FIG. 3 is a flowchart showing the procedures of the semiconductor inspection method according to the embodiment.

First, the semiconductor device S which is an inspection object is observed in a state where the solid immersion lens 3 is set at the standby position off the optical axis. Herein, the image acquiring part 1 acquires a pattern image of the circuit pattern which is an observation image of the semiconductor device S through the optical system 2 containing the objective lens 20 (S101) The inspection part 16 controls the semiconductor device S to a prescribed state, and an abnormality observation image for detecting the abnormal position of the semiconductor device S is acquired (S102).

Next, whether the abnormal position exists in the semiconductor device S is examined by using the pattern image and the abnormality observation image acquired by the image acquiring part 1. If there is an abnormal position, the position thereof is detected, and the abnormal position detected is set as the inspection position by the semiconductor inspection apparatus (S103, inspection setting step). The image acquiring part 1 and the optical system 2 are moved by the XYZ stage 15 so that the set inspection position is located at the center of the image acquired by the image acquiring part 1.

Then, the solid immersion lens 3 is set at the observation position on the substrate corresponding to the inspection position judged to be an abnormal position in the semiconductor device S, and the solid immersion lens is inserted between the semiconductor device S and the objective lens 20. At this time, the operator drips an optical contact liquid onto the observation position before setting the solid immersion lens 3 (S104) to wet the observation position. The optical contact liquid is comprised of an amphipathic molecule (for instance, a surfactant molecule) contained in water. Since the optical contact liquid contains the amphipathic molecule, the optical contact liquid lowers the surface tension on the semiconductor substrate which is the hydrophobic surface. As a result, the wettability on the hydrophobic surface is improved, and thereby the optical contact liquid is spread on the semiconductor device S.

Figure 4A:
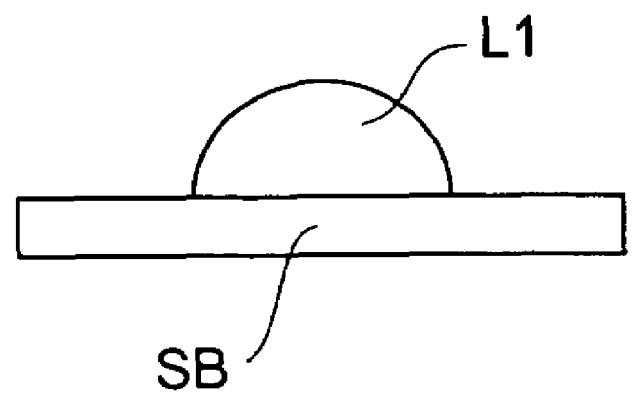
FIG. 4A is a view schematically showing the state of water which does not contain an amphipathic molecule dripped onto the surface of a substrate.

Herein, the relationship between the semiconductor device S and the optical contact liquid will be described. For instance, when the water or the like used as a solvent of the optical contact liquid is used for the optical contact, since the surface tension of water is very large, as shown in FIG. 4A, a droplet L1 is shaped in hemisphere on a substrate SB. Therefore, when the surface accuracy of the substrate SB is high, the droplet L1 is slid down on the substrate SB by tilting the substrate slightly.

The droplet is turned into a spherical shape in which the surface area is smallest by the surface tension as the volume of the droplet of water becomes small. On the other hand, since the solid immersion lens 3 for which the diameter is 1 to 5 mm is an extremely small optical element and the volume of the optical contact liquid required is very small, the droplet becomes extremely small. It is very difficult to hold the above small droplet in a desired position on a slippery hydrophobic surface.

Figure 4B:
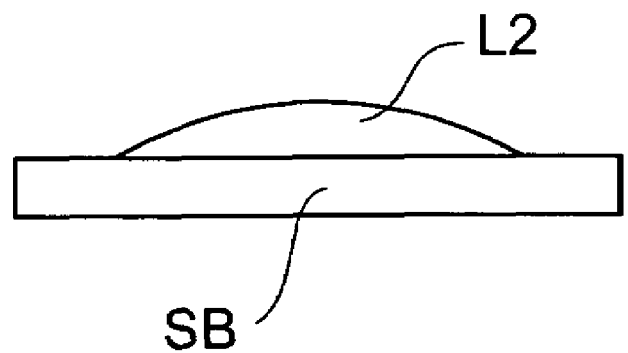
FIG. 4B is a view schematically showing the status of water containing an amphipathic molecule dripped onto the surface of a substrate.

On the other hand, the optical contact liquid according to the embodiment contains an amphipathic molecule. When the optical contact liquid containing the above amphipathic molecule is dripped onto the semiconductor substrate which is the hydrophobic surface, the amphipathic molecule contained in the droplet comprised of the optical contact liquid reduces the surface tension of the droplet. Therefore, the wettability on the semiconductor substrate composed of the hydrophobic surface is improved, and the droplet L2 is spread on the substrate SB as shown in FIG. 4B. Thus, the optical contact liquid can be adequately held in a desired observation position on a substrate for which the surface is a hydrophobe by the application of the wettability to the hydrophobic surface due to the amphipathic molecule. In general, the above optical contact liquid can be suitably used for bringing the solid immersion lens into optically-close contact with the sample when the sample is observed.

A surfactant molecule is preferably used as the amphipathic molecule used herein. An ionic surfactant molecule and a nonionic surfactant molecule can be used as the surfactant molecule. A cationic surfactant molecule, an anionic surfactant molecule and an amphoteric surfactant molecule can be used as the ionic surfactant molecule.

Though the surfactant is usually used for various usages as a humectant, a penetrant, a foaming agent, a defoaming agent, an emulsifying agent, and an antistatic agent or the like, it is suitable that the surfactant has defoaming property and antistatic property in addition to wettability in the present invention. The suctioning of air due to electrification can be prevented by using the surfactant having antistatic property. The generation of bubbles due to mechanical transportation or stirring when the optical contact liquid is supplied can be prevented by using the surfactant having the defoaming property.

The optimal concentration of the surfactant is suitably within the range of more than 0 and no more than 400 times to the critical micelle concentration of the surfactant. When the concentration ratio is more than 400, the viscosity of the optical contact liquid tends to increase excessively, and thereby the optical contact may be obstructed.

The concentration range is more preferably within the range of 0.5 to 100 times to the critical micelle concentration of the surfactant. When the concentration ratio is less than 0.5 times, the surface tension of the optical contact liquid tends not to be sufficiently reduced. When the concentration ratio is more than 100 times, the viscosity of the optical contact liquid tends to increase excessively. The concentration range is more preferably within the range of 1 to 10 times to the critical micelle concentration of the surfactant due to similar reasons.

The optical contact liquid used in the embodiment is not limited to the one containing the surfactant molecule, optical contact liquids containing both a hydrophilic group (a carboxyl group, a sulfo group, a quaternary ammonium group, and a hydroxyl group or the like) and a hydrophobic group (referred to as an oleophilic group, a long-chain hydrocarbon group or the like) may be used. Examples of the optical contact liquids include a lubricant such as glycerin, propyl glycogen and sorbitol; a phosphatide; a glycolipid; and an amino lipid.

For instance, as an optical coupling material for optically coupling the semiconductor substrate to the solid immersion lens, refractive index matching fluid (index matching liquid or the like) described in Japanese Patent Publication No. H7-18806 is known. This technique uses the refractive index matching, and the refractive index matching liquid is essentially different from the optical contact liquid according to the present invention. The former achieves high NA by using the refractive index of liquid, and the latter plays the role of assisting in evanescent coupling.

When the optical contact liquid is spread on the semiconductor device S, the solid immersion lens 3 standing by at a position off the optical axis is moved by the solid immersion lens driving part 30 before the optical contact liquid is dried, and the solid immersion lens 3 is set on the optical contact liquid (S105, a lens setting step). When solid immersion lens 3 is set, the self-weight of the solid immersion lens 3 is used. Thus, the solid immersion lens 3 is set on the optical contact liquid in the inspection position, and the solid immersion lens 3 is inserted between semiconductor device S and the objective lens 20. Herein, the optical contact liquid can apply the wettability to the mounting surface of the solid immersion lens 3 since the optical contact liquid contains the amphipathic molecule. Therefore, the small solid immersion lens 3 can be easily set without applying excessive pressure to a desired position on the semiconductor substrate.

After the solid immersion lens 3 is inserted between semiconductor device S and the objective lens 20, the inserted position of the solid immersion lens 3 is adjusted (S106, a position adjusting step). First, the image containing a reflected light from the solid immersion lens 3 is acquired by the image acquiring part 1. The adjustment of the inserted position of the solid immersion lens 3 is performed by using the reflected light from the reflection surface of each part of the solid immersion lens 3 in the reflected light image contained in the image as a guide.

When the inserted position of the solid immersion lens 3 is adjusted, the image containing the reflected light from the solid immersion lens 3 is analyzed automatically or based on the instruction of an operator in the image analysis part 61, thereby the position of the center of gravity of the reflected light image is determined. The instructing part 62 instructs the adjustment of the inserted position of the solid immersion lens 3 so that the position of the center of gravity of the reflected light image obtained by the image analysis part 61 coincides with the inspection position in the semiconductor device S with respect to the solid immersion lens 3 and the solid immersion lens driving part 30 through the solid immersion lens control part 53. As a result, the solid immersion lens 3 is aligned to the semiconductor device S and the objective lens 20.

In addition, the instructing part 62 instructs the adjustment of the distance between the semiconductor device S with which the solid immersion lens 3 is brought into close contact and the objective lens 20 of the optical system 2 with respect to the XYZ stage 15 through the stage control part 52, together with the adjustment of the inserted position of the above solid immersion lens 3 (S107, a distance adjusting step). As a result, focusing is performed in the state where the solid immersion lens 3 is inserted.

After the focusing is performed, the optical contact liquid is evaporated and dried by spraying air in the state where the solid immersion lens 3 is aligned, and the solid immersion lens 3 is brought into optically-close contact with the semiconductor device S (S108, a lens contacting step). Since the optical contact liquid contains the amphipathic molecule in the embodiment, it is possible to bring the solid immersion lens 3 into optically-close contact with the semiconductor device S securely. A means for absorbing the optical contact liquid by using an absorbing sheet such as a paper or the like can be used in addition to a means for spraying air as a means for promoting the drying of the optical contact liquid. When the optical contact liquid is thinly applied, the drying thereof is fast, and thereby the work for promoting the drying can be omitted.

At the step where the optical contact liquid is dried, the optical contact liquid may be slightly left around the solid immersion lens 3, and the optical contact liquid can be naturally dried after minute adjustment so that the position can be minutely adjusted.

Figure 5A:
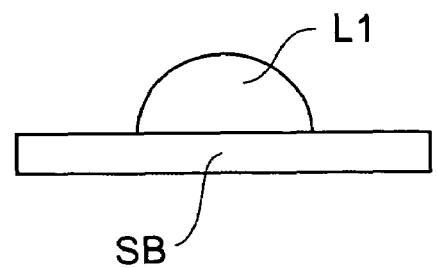
FIG. 5A to FIG. 5D are views schematically showing the change with time after water which does not contain an amphipathic molecule is dripped onto the surface of a substrate.

Herein, when only water of the solvent of the optical contact liquid is used for example, a hemispherical droplet L1 is formed on an Si substrate SB as shown in FIG. 5A. Though it is difficult to hold this droplet L1 in the inspection position as described above, the droplet L1 is assumed to be held in the inspection position.

Figure 5B:
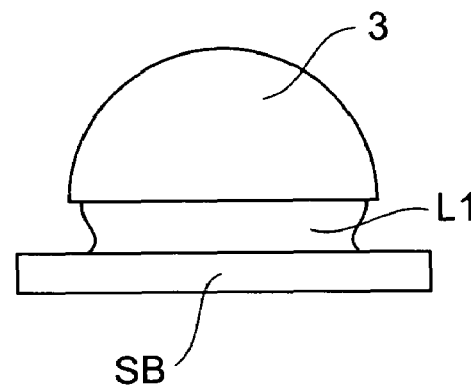
Figure 5C:
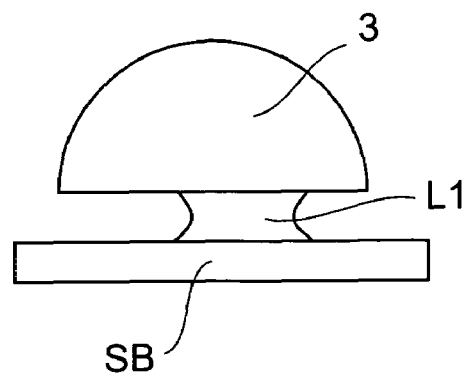
Figure 5D:
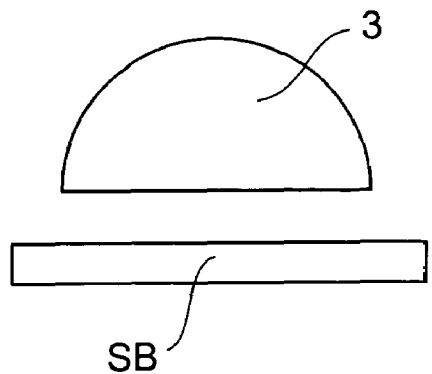

If the solid immersion lens 3 is set on the droplet L1 as shown in FIG. 5B, the power lowering the surface area of the droplet L1 becomes dominant, and the wettability of the Si substrate SB and the solid immersion lens 3 cannot be maintained. Therefore, as shown in FIG. 5C, air penetration progresses before a surface interval is sufficiently narrowed, and the size of the droplet L1 becomes gradually small. Finally, as shown in FIG. 5D, the optical contact cannot be obtained.

Figure 6A:
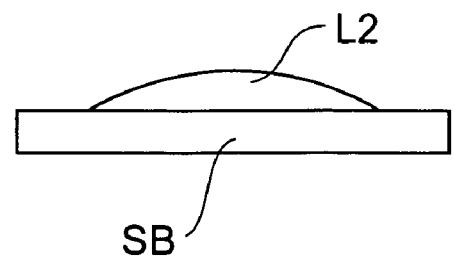
FIG. 6A to FIG. 6D are views schematically showing the change with time after water containing an amphipathic molecule is dripped onto the surface of a substrate.
Figure 6B:
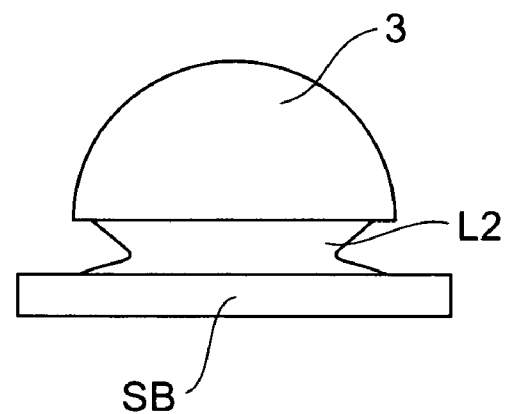
Figure 6C:
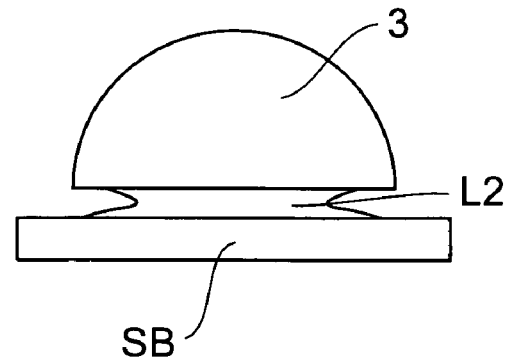
Figure 6D:
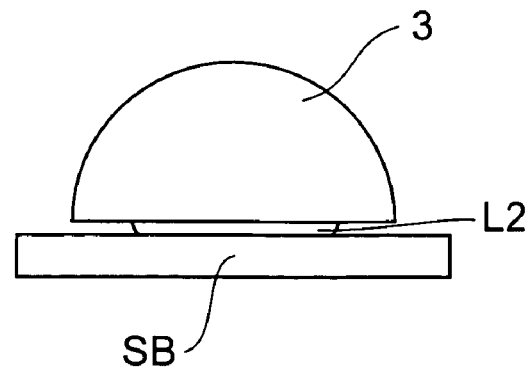

On the other hand, when the optical contact liquid which contains the amphipathic molecule and has low surface tension is used, a liquid droplet L2 is spread on the Si substrate SB as shown in FIG. 6A. When this droplet L2 is dried, power keeping the wettability of the surface of the Si substrate SB and the bottom (mounting surface) of the solid immersion lens 3 becomes dominant. Therefore, as shown in FIG. 6B, the volatilization of water of the droplet L2 mainly progresses during the process of obstructing the air penetration while the surface interval between the bottom of the solid immersion lens 3 and the surface of the Si substrate SB is narrowed. Afterwards, the volatilization of the droplet L2 progresses while obstructing the penetration of air as shown in FIG. 6C, and finally, the solid immersion lens 3 is brought into optically-close contact with the Si substrate SB as shown in FIG. 6D.

Figure 7:
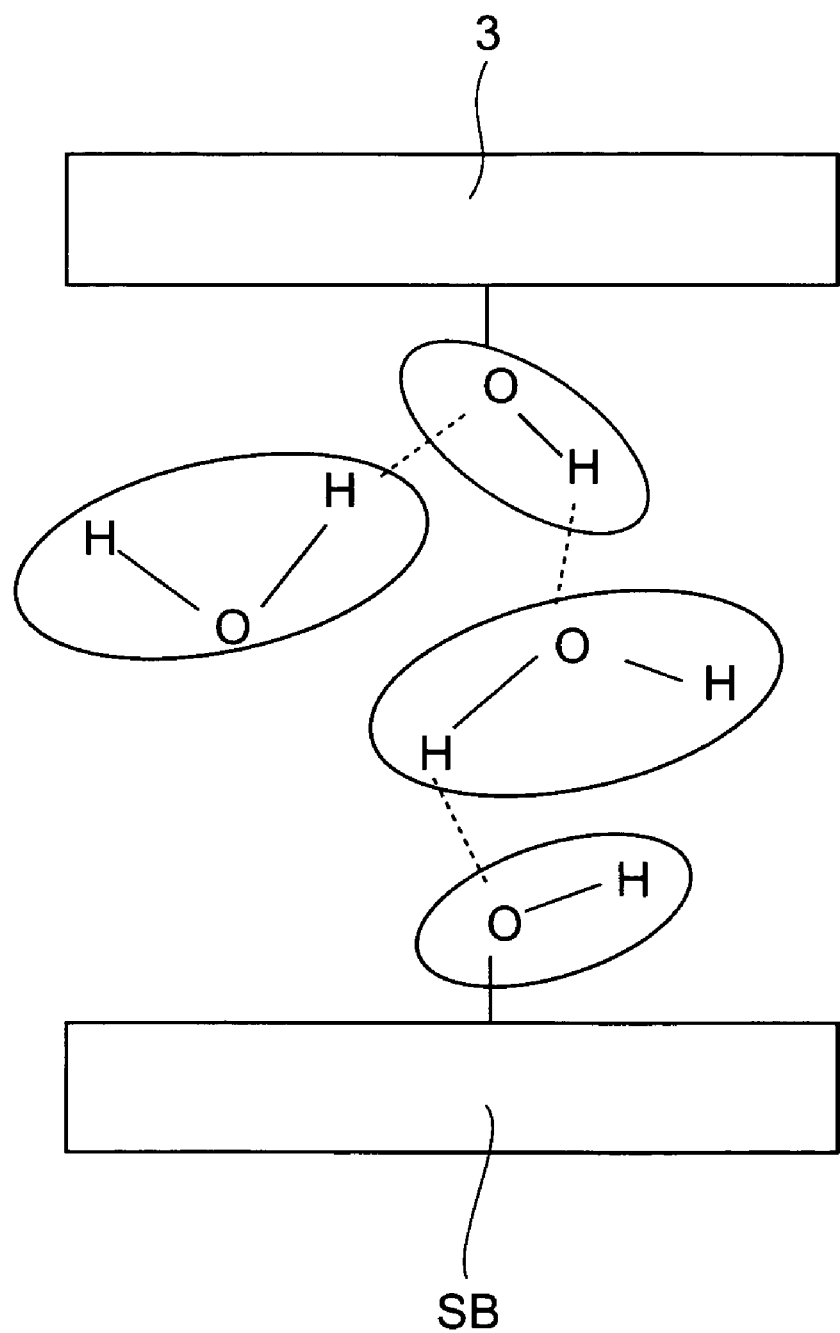
FIG. 7 is a view schematically showing the close-contact state of a solid immersion lens to a substrate.

Under such a condition, as shown in FIG. 7, van der Waals force acts between the hydrophilic group of the amphipathic molecule physically adsorbed to the Si substrate SB and the water molecule, and the volatilization is stopped by restraining the water molecule. At this time, the distance between the solid immersion lens 3 and the Si substrate SB can be made $\frac{1}{20}\lambda$ ($\lambda$: irradiation wavelength) or less, and as a result, the optical contact between the solid immersion lens 3 and the Si substrate SB, and the physical fixing can be achieved.

Thus, after the solid immersion lens 3 is brought into optically-close contact with the semiconductor device S, the image acquiring part 1 acquires the magnified observation image of the semiconductor device S through the optical system 2 containing the objective lens 20 and the solid immersion lens 3 set on the semiconductor device S (S109, an image acquiring step).

After the magnified observation image is acquired, the solvent of the optical contact liquid (hereafter, referred to as "solvent") is dripped around the position in which the solid immersion lens 3 is fixed in the semiconductor device S (S110), and the fixing position of the solid immersion lens 3 is made wet. This solvent is penetrated between the semiconductor device S and the solid immersion lens 3 by dripping the solvent, and the optical contact and the physical fixing between the semiconductor device S and the solid immersion lens 3 are released.

Thus, the physical fixing between the semiconductor device S and the solid immersion lens 3 is released by using the solvent, and thereby the semiconductor device S can be prevented from damage since the solid immersion lens 3 can be peeled off by very weak power. Since the solid immersion lens 3 can also be prevented from damage, the solid immersion lens 3 can be reused. Herein, the solvent is dripped. However, even when the optical contact liquid is dripped, the optical contact and the physical fixing between the semiconductor device S and the solid immersion lens 3 can be released without damaging the semiconductor device S and the solid immersion lens 3.

Thus, after the inspection position is inspected, the solid immersion lens 3 is moved to another inspection position or the standby position, and the inspection of the inspection position is ended.

When the solid immersion lens 3 is aligned by using the image containing the reflected light from the solid immersion lens 3, it is preferable that specifically, as described above, the position of the center of gravity of the reflected light image from the solid immersion lens 3 is determined, and it is preferable that the position where the solid immersion lens 3 is inserted is adjusted so that the center position thereof coincides with the inspection position of semiconductor device S. As a result, the solid immersion lens 3 can securely be aligned. Or, another method for aligning may be used. For instance, the inserted position of the solid immersion lens 3 may be adjusted so that the position of the center of gravity of the reflected light image from the solid immersion lens 3 coincides with that of the center of gravity of the inspection position in the semiconductor device S.

When the semiconductor device S is inspected by using the solid immersion lens 3, the inspection position of the semiconductor device S is preferably set to the center of the image acquired by the image acquiring part 1. As a result, the pupil of the objective lens 20 can be effectively used for observing the semiconductor device S.

That is, when solid immersion lens 3 is used, only a part of the pupil of the objective lens 20 is used, and the use position is changed in accordance with the field angle. Therefore, the usability of light becomes highest by setting the solid immersion lens 3 on the optical axis of the objective lens 20. The deterioration in the uniformity of the brightness of the image generated in the solid immersion lens 3 can be reduced in the above setting of the solid immersion lens 3.

In the semiconductor inspection apparatus shown in FIG. 1, the XYZ stage 15 is set for the image acquiring part 1 and the optical system 2 so as to align the image acquiring part 1 and the optical system 2 and focus them to the semiconductor device S. The XYZ stage may be used as the stage 18 on which the semiconductor device S is placed. A θ-stage is structured to be movable in the angular direction may be further set.

The amphipathic molecule is contained in the optical contact liquid interposed between the semiconductor device S and the solid immersion lens 3 in the above embodiment. Instead, the hydrophilic treatment may be applied to the mounting surface of the solid immersion lens 3 to the semiconductor device S.

The improvement in the wettability due to the amphipathic molecule contained in the optical contact liquid is caused by the fact that a hydrophilic group is adhered to the surface which is a hydrophobe. Therefore, in the case where the optical contact liquid does not contain the amphipathic molecule, even when the mounting surface of the solid immersion lens 3 with the semiconductor device S and the mounting surface of the semiconductor device S with the solid immersion lens 3 are a hydrophobe, the wettability can be improved by treating at least one or both of these surfaces with a hydrophilic treatment adhering the hydrophilic group. When the surface of the semiconductor device S is originally hydrophilicity, the wettability of the surface thereof can be secured even when a hydrophilic treatment is not subjected to the surface.

Thus, the wettability is applied to one or both of the mounting surfaces of the solid immersion lens 3 and the semiconductor device S, thereby the optical contact liquid can be adequately held at a desired inspection position on the substrate of the semiconductor device S in the same manner as the case of using the optical contact liquid containing the amphipathic molecule. The optical contact between the semiconductor device S and the solid immersion lens 3 can be securely obtained without applying excessive pressure. Furthermore, the physical fixing can also be obtained between the semiconductor substrate and the solid immersion lens.

Examples of methods for treating the solid immersion lens 3 and the semiconductor device S with a hydrophilic treatment include a method for allowing a hydrophilic group to adsorb physically and adhere temporarily. Specific examples of methods for allowing the hydrophilic group to adsorb physically include a method for applying a surfactant or a solution containing an amphipathic molecule such as amino acid and protein on a surface to which the hydrophilic treatment is applied and drying the applied solution.

Examples of methods for applying the hydrophilic treatment also include a method for allowing a hydrophilic group to adsorb chemically and performing a surface reforming. Examples of methods for making the hydrophilic group adsorb chemically include a method for irradiating UV (ultraviolet) light, a wet process (for instance, a solution obtained by mixing sulfuric acid, hydrogen peroxide and water is applied), and a dry process (for instance, an ion beam is irradiated) or the like. For instance, semicoclean 23 (manufactured by FURUUCHI CHEMICAL CORPORATION) can be used for the hydrophilic process due to the chemical adsorption in the wet process.

A coating method can be used as another method for applying the hydrophilic treatment. In this case, hydrophilicity nanoparticles or the like are preferably coated on the surface. For instance, nanoparticles of silica are coated on one or both of the solid immersion lens and the semiconductor substrate, thereby the wettability thereof can be improved. Examples of the above nanoparticles include GLANZOX3900 (manufactured by FUJIMI INCORPORATED) and a dewing water droplet inhibitor (manufactured by TOTO).

The nanoparticles or the like of titanium oxide may be coated in addition to the nanoparticles of silica. Since an excessively thick coating film may prevent the optical evanescent coupling from being obtained when the hydrophilic treatment is applied by the above coating, it is necessary to be careful. Therefore, it is preferable that the coating film is set to 200 nm or less.

Figure 8:
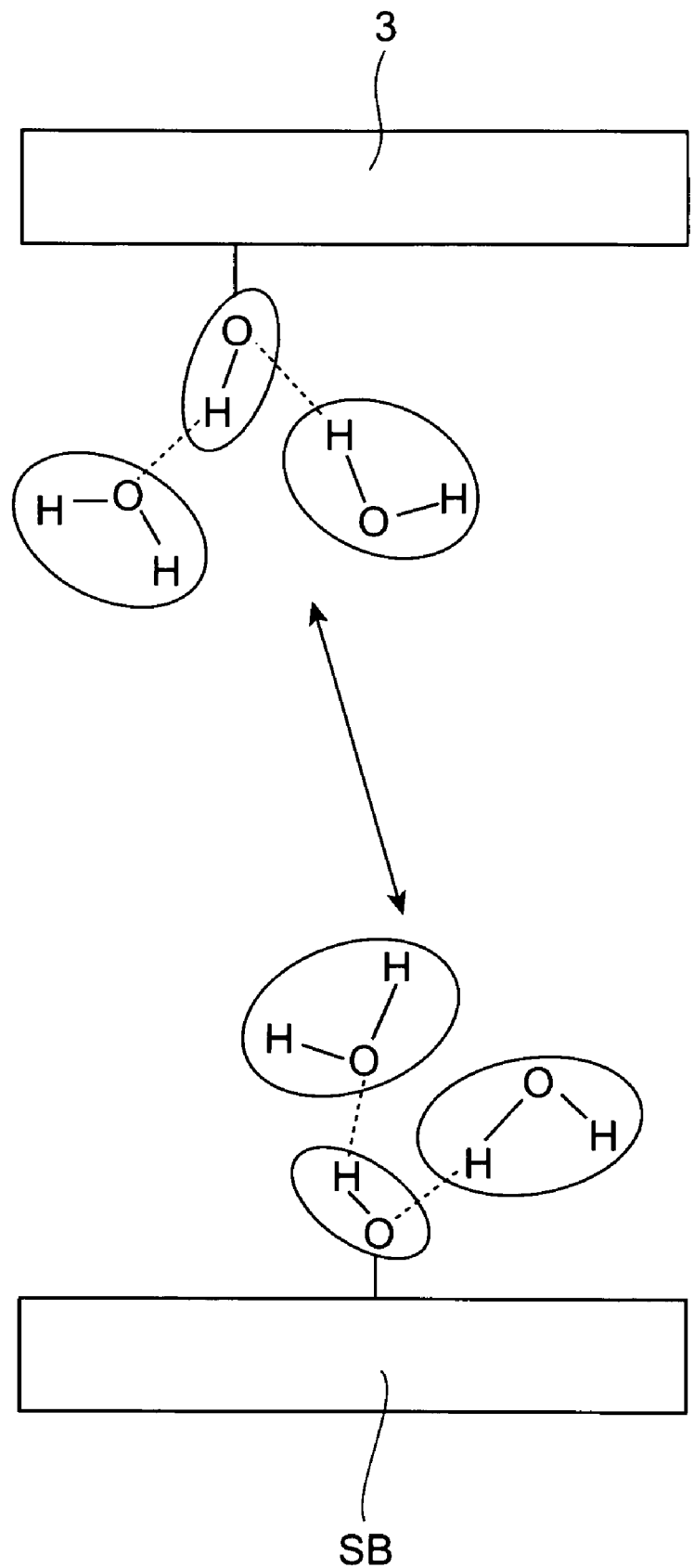
FIG. 8 is a view schematically showing the closely contacting process of a solid immersion lens to a substrate.

When the solid immersion lens and the surface of the substrate are treated with a hydrophilic treatment, as shown in FIG. 8, water molecules in the atmosphere are always adsorbed to the hydrophilic groups, and so to speak, the water film is formed. When the solid immersion lens 3 and the substrate SB are sufficiently brought close in this state, an attraction force due to the hydrogen bond acts between the water molecules, and thereby the close contact between the solid immersion lens 3 and the substrate SB is achieved.

When the solid immersion lens and the substrate surface are sufficiently treated with a hydrophilic treatment, and the surface accuracy is sufficiently high, the close-contact is achieved only by overlapping these surfaces mutually. Herein, the distance where the attraction force due to the hydrogen bond acts is very short such as about several nm. Therefore, when the solid immersion lens and the substrate surface are insufficiently treated with a hydrophilic treatment, or the surface accuracy is insufficient, the contact may be not sufficiently achieved among the surfaces.

Figure 9:
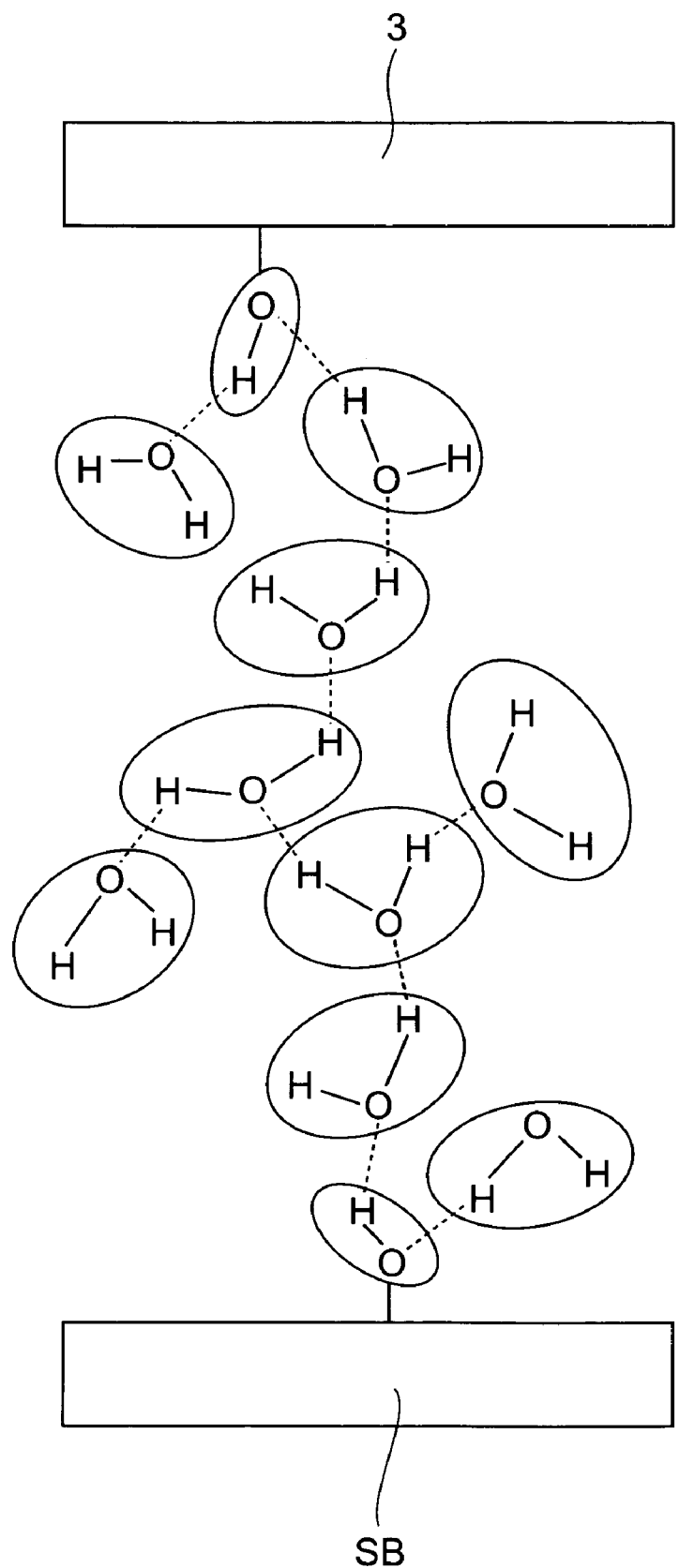
FIG. 9 is a view schematically showing the closely contacting process of a solid immersion lens to a substrate.

For this case, as shown in FIG. 9, it is desirable to use the optical contact liquid for assisting the close-contact (see FIG. 6B). Herein, the case where the main component of the optical contact liquid is water will be described. In this case, when the interface between the solid immersion lens and the substrate is filled with the optical contact liquid, the solid immersion lens and the substrate are connected through the hydrogen bond of the hydroxyl group and the water molecule. However, since the interval between the solid immersion lens 3 and the substrate SB is wide under this condition as shown in FIG. 9, the contact is not yet achieved. Afterwards, the attraction force due to the hydrogen bond acts between the solid immersion lens and the substrate in a process where extra moisture is volatilized. As a result, the interval of the interface is gradually narrowed with the volatilization of the liquid, and the volatilization of the optical contact liquid is stopped when the close-contact state is achieved.

When the solid immersion lens and the substrate are not treated with a hydrophilic treatment, and the surfactant is not added to the optical contact liquid, the hydrogen bond does not act among the solid immersion lens, the substrate, and the water molecule. Therefore, the solid immersion lens, the substrate, and the water molecule are separated in the process in which water is volatilized, and air flows in. Thereby the close-contact is not achieved (see FIG. 5A to FIG. 5D).

On the other hand, in the case where the solid immersion lens and the substrate are not previously treated with a hydrophilic treatment, and the surfactant is added to the optical contact liquid, when the optical contact liquid is inserted between the solid immersion lens and the substrate, the surfactant, that is, the hydrophilic group is physically adsorbed to the solid immersion lens and the substrate. As a result, the solid immersion lens and the substrate has the same state as the case where the solid immersion lens and the substrate are previously treated with a hydrophilic treatment, and thereby the close-contact can be achieved.

Though the preferred embodiment of the present invention has been described, the present invention is not limited to the above embodiment. For example, though the operator drips the optical contact liquid in the above embodiment, as shown schematically in FIG. 1, an optical contact liquid dripping apparatus 81 is preferably arranged. An air blower 82 for drying the optical contact liquid may be further arranged. Or, a water absorbing sheet pressing apparatus or the like may be arranged. Though the optical contact liquid dripping apparatus 81 drips the optical contact liquid in general, as described above, the optical contact liquid dripping apparatus 81 is used for dripping the optical contact liquid containing the amphipathic molecule in a necessary case where the mounting surface of the solid immersion lens is not treated with a hydrophilic treatment, for example.

In addition, various methods such as a method for thinly spreading and coating the optical contact liquid, a method for spraying and a method for wetting by steam in addition to a method for dripping the optical contact liquid can be used as a means for wetting the semiconductor device. In this case, since the optical contact liquid is quickly dried, the work for promoting drying can be omitted.

In addition to the semiconductor inspection apparatus shown in the above embodiment, the sample observation method of the present invention, the microscope, the solid immersion lens, and the optical contact liquid can be used when the sample is observed by an emission microscope using a high sensitivity camera, an OBIRCH analysis device, a time-resolved emission microscope, and a heat ray image analysis device or the like.

The semiconductor inspection apparatus which makes the semiconductor device an observation object, and the method of inspecting the semiconductor are described in the above embodiment. However, when the one excluding the semiconductor device is made the sample, the present invention can be applied as a sample observation method for observing a sample to obtain the internal information, the microscope, the solid immersion lens, and the optical contact liquid. As a result, the fine structure or the like of the sample can be easily observed when observing the sample.

For example, though the sample of the observation object is made the semiconductor device in the embodiment, when various electronic devices such as the semiconductor device are made the sample in general, the device as the object is not limited to the one using the semiconductor substrate. An integrated circuit using a glass or a plastic or the like as the substrate such as a polysilicon thin film transistor may be made the observation object. For instance, the device is formed on a glass substrate in a liquid crystal device, or the device is formed on a plastic substrate in an organic EL. Examples of general samples include a bio-related sample or the like using a preparation in addition to various devices such as the above-described semiconductor device and the liquid crystal device.

Next, though examples of the present invention will be described, the present invention is not limited to the examples.

EXAMPLE 1

In Example 1, the experiment was performed by using a semiconductor device having an Si substrate as a semiconductor device as an inspection object. In the experiment, optical contact liquid obtained by adding a surfactant to pure water was used. As the surfactant, "Olfin EXP. 4001" (manufactured by Nisshin Chemical Industry Co., Ltd.) which was a nonionic surfactant was used.

The experiment was performed according to the following procedure. The rear surface of the semiconductor device was observed by the semiconductor inspection apparatus shown in the above embodiment after the optical contact liquid was placed between the substrate of the semiconductor device and the solid immersion lens, and extra moisture was dried, and the brightness value of the semiconductor device was measured. The concentration ratio of the surfactant to the critical micelle concentration was changed, and measurement of the brightness value was repeated ten times. The mean value of the measurement values corresponding to the concentration ratios of surfactants measured to the critical micelle concentration was determined. The brightness value herein is due to a confocal laser scan image, and the maximum brightness value when focus is coincided. The concentration ratio to the critical micelle concentration is the numerical value showing how many times the critical micelle concentration corresponds.

Figure 10:
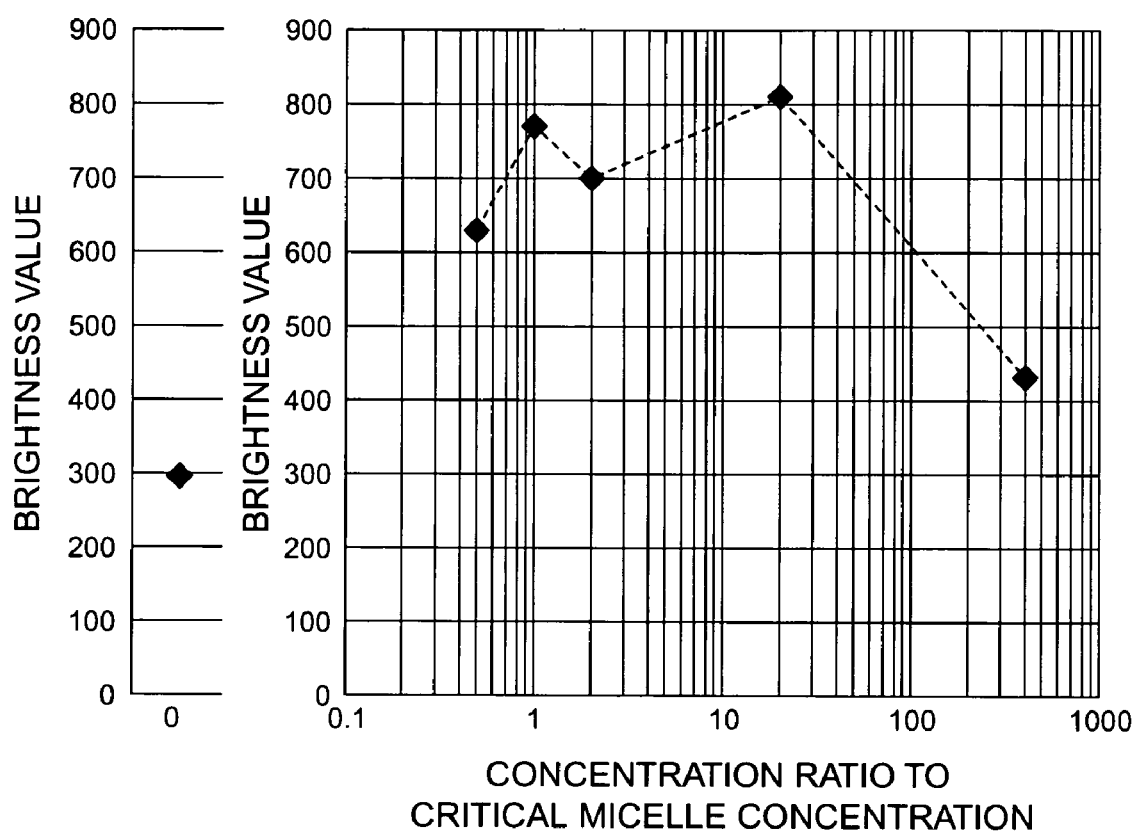
FIG. 10 is a graph showing the relationship between the concentration ratio of a surfactant molecule contained in optical contact liquid to the critical micelle concentration of a nonionic surfactant molecule and the brightness value of an electronic device for which the rear surface is observed.

Thus, the mean value of the brightness values corresponding to the concentration ratios to critical micelle concentrations acquired is shown in FIG. 10.

As shown in FIG. 10, when the concentration ratio to the critical micelle concentration was 0, that is, the optical contact liquid which did not contain the surfactant was used, the average of the brightness values measured was about 300. When the concentration ratio to the critical micelle concentration was 0.5, the mean value of the brightness values was about 620, and the brightness value was improved than in the case where the optical contact liquid which did not contain the surfactant was used. Therefore, it is found that the optical close-contact degree between the solid immersion lens and the semiconductor device can be improved by using the optical contact liquid containing the surfactant.

Furthermore, surplus surfactant remains as contamination when the concentration ratio to the critical micelle concentration is about 1. However, as shown in FIG. 10, even when the concentration ratio to the critical micelle concentration was about 1, the mean value of the brightness values was about 790, and did not lower. As soon, the mean value was improved, it was found that the level did not obstruct when the solid immersion lens was brought into optically-close contact with the semiconductor device. When the concentration ratio to the critical micelle concentration exceeds 100, the surplus surfactant becomes a large amount. Therefore, the mean value of the brightness values lowers to about 410, and is considered to obstruct when the solid immersion lens is brought into optically-close contact with the semiconductor device.

After the solid immersion lens is brought into optically-close contact with the semiconductor device by the optical contact liquid containing the surfactant, when the optical contact between the solid immersion lens and the semiconductor device is released, the hydrophilicity remains at the position in which the solid immersion lens is brought into close contact with the semiconductor device (not shown in the graph) Therefore, the position in which the solid immersion lens is brought into close contact with the semiconductor device is treated with a hydrophilic treatment, and has hydrophilicity. Therefore, until hydrophilicity is lost at the position in which the optical contact is formed once by using the surfactant, the solid immersion lens is securely brought into optically-close contact with the semiconductor device by, for instance, pure water which does not contain the surfactant.

The solid immersion lens is also similar, and the mounting surface of the solid immersion lens brought into optically-close contact with the semiconductor device once is treated with a hydrophilic treatment, and has hydrophilicity. Therefore, until hydrophilicity is lost, the solid immersion lens is securely brought into optically-close contact with the semiconductor device by, for instance, pure water which does not contain the surfactant.

EXAMPLE 2

In Example 2, the experiment was performed by using a semiconductor device having an Si substrate as a semiconductor device as an inspection object. In the experiment, optical contact liquid obtained by adding a surfactant to pure water was used. As the surfactant, "Olfin PD-301" (manufactured by Nisshin Chemical Industry Co., Ltd.) which was an ionic surfactant was used.

The experiment was performed according to the following procedure. The rear surface of the semiconductor device was observed by the semiconductor inspection apparatus shown in the above embodiment after the optical contact liquid was interposed between the substrate of the semiconductor device and the solid immersion lens, and extra moisture was dried, and the brightness value of the semiconductor device was measured. The concentration ratio of the surfactant to the critical micelle concentration was changed, and measurement of the brightness value was repeated five times. The mean value of the measurement values corresponding to the concentration ratios of surfactants measured to the critical micelle concentration was determined. The brightness value herein is due to the confocal laser scan image, and the maximum brightness value when focus is coincided.

Figure 11:
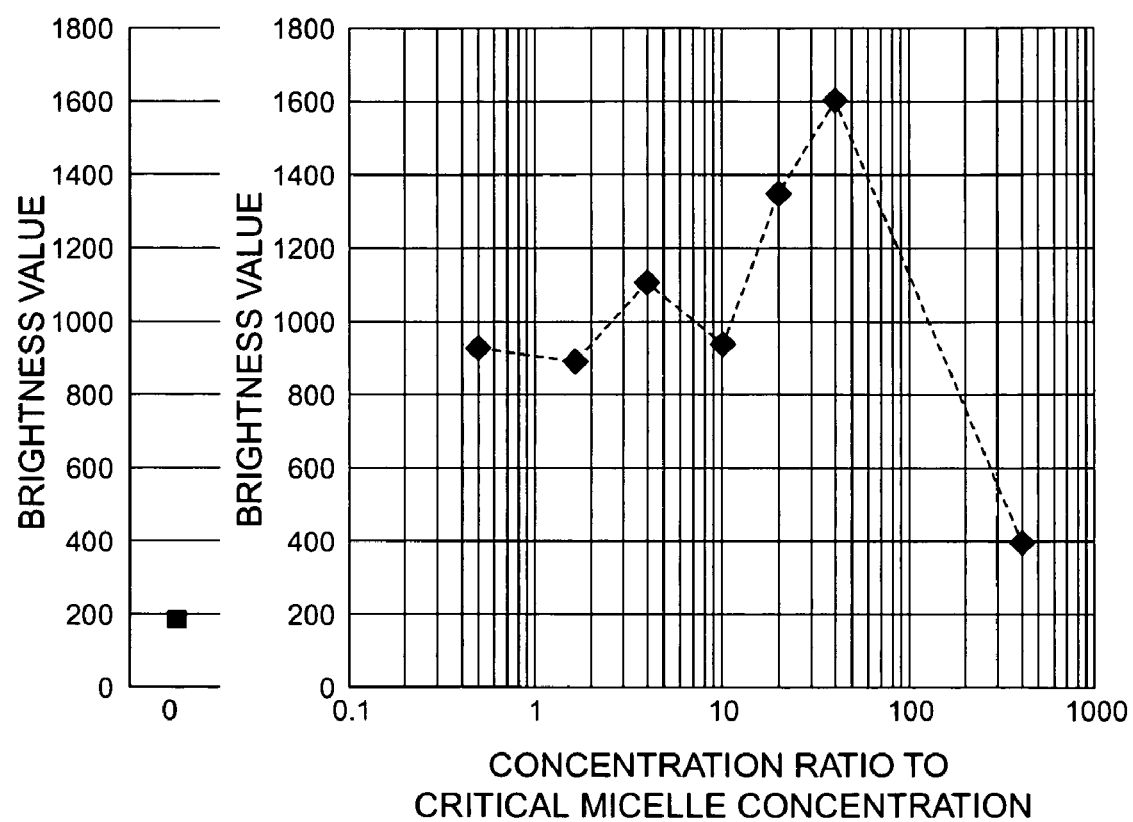
FIG. 11 is a graph showing the relationship between the concentration ratio of a surfactant molecule contained in optical contact liquid to the critical micelle concentration of an ionic surfactant molecule and the brightness value of an electronic device for which the rear surface is observed.

Thus, the mean value of the brightness values corresponding to the concentration ratios to critical micelle concentration obtained is shown in FIG. 11.

As shown in FIG. 11, when the concentration ratio to the critical micelle concentration was 0%, that is, the optical contact liquid which does not contain the surfactant was used, the average of the brightness values measured was about 190. On the other hand, when the concentration ratio to the critical micelle concentration was 0.5, the brightness value was about 950, and the brightness value was improved than in the case where the optical contact liquid which did not contain the surfactant was used. Therefore, even when the optical contact liquid containing the surfactant composed of the ionic surfactant is used, the optical close-contact degree between the solid immersion lens and the semiconductor device can be improved.

When the concentration ratio to the critical micelle concentration exceeds 100, and is about 400, the mean value of the brightness values is about 400. This is caused because the surplus surfactant remains as contamination in the same manner as Experiment 1, and obstructs the optical contact between the semiconductor device and the solid immersion lens. Therefore, the concentration ratio to the critical micelle concentration is suitably 100 or less even when the ion surfactant is used.

EXAMPLE 3

In Example 3, the experiment was performed by using a semiconductor device having an Si substrate as a semiconductor device as an inspection object. In the experiment, optical contact liquid obtained by adding a surfactant to pure water was used. As the surfactant, "Olfin EXP. 4001" (manufactured by Nisshin Chemical Industry Co., Ltd.) which was a nonionic surfactant was used in the same manner as Example 1. Though an aqueous solution of a glutamic acid which is one of the amino acids is used in this experiment, the amino acid extracted from protein can be used. The concentration of the glutamic acid solution was set to 10%.

The experiment was performed according to the following procedure. First, the glutamic acid solution is applied on the substrate of the semiconductor device and is dried. Then, the optical contact liquid for which the critical micelle concentration of the surfactant was 0.05% was interposed between the solid immersion lens and the substrate of the semiconductor device. Extra liquid was dried, the rear surface of the semiconductor device was observed by the semiconductor inspection apparatus described in the above embodiment, and the brightness value of the semiconductor device was measured. This brightness value was measured 20 times, and the mean value was determined.

Figure 12:
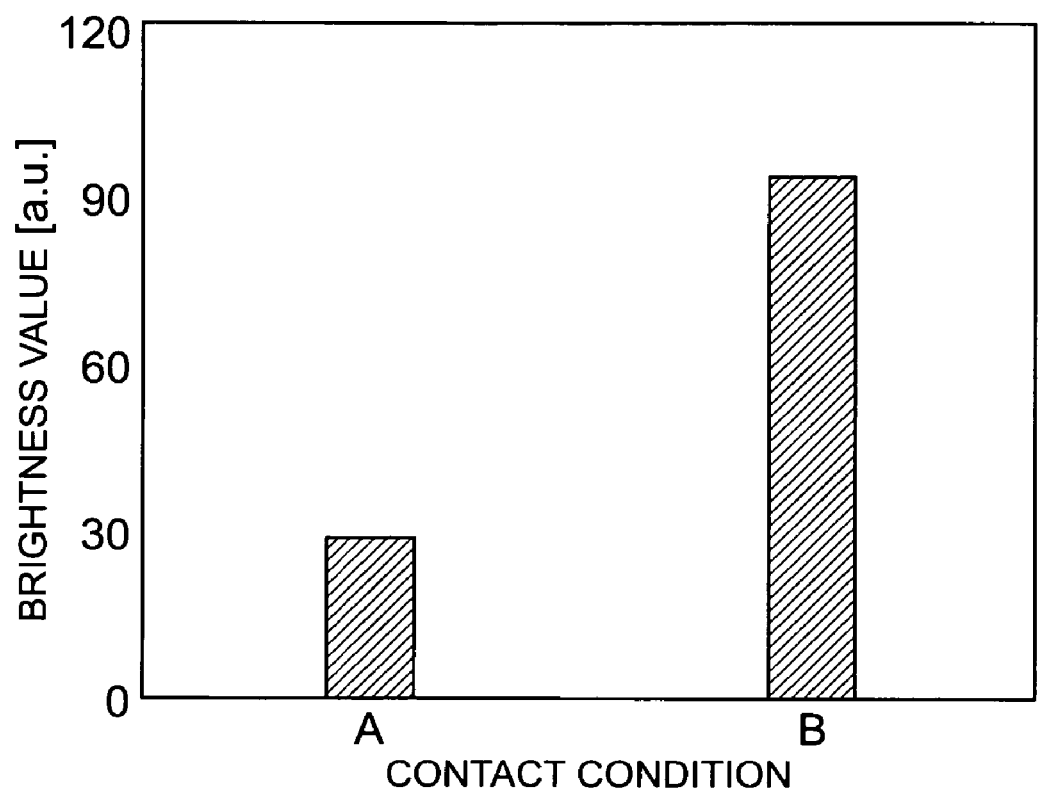
FIG. 12 is a graph showing the brightness values of electronic devices when a glutamic acid solution is applied on an electronic device and when a glutamic acid solution is not applied on an electronic device, respectively.

In addition, the optical contact liquid for which the critical micelle concentration of the surfactant was 0.05% was interposed between the solid immersion lens and the substrate of the semiconductor device without applying the glutamic acid on the semiconductor device. Extra liquid was dried, the rear surface of the semiconductor device was observed by the semiconductor inspection apparatus described in the above embodiment, and the brightness value of the semiconductor device was measured. This brightness value was measured 20 times, and the mean value was calculated. FIG. 12 shows the results.

As shown in FIG. 12, the average A of the brightness value was about 30 in the example in which the glutamic acid solution was not applied. On the other hand, the average B of the brightness value was about 90 in the example in which the glutamic acid was applied. Thus, since the average of the brightness value was improved by applying the glutamic acid, the wettability of the substrate of the semiconductor device was improved in appearance, and the optical contact between the semiconductor device and the solid immersion lens was able to be improved. This means that the wettability on the hydrophobic surface is improved by giving the hydrophilic group to the hydrophobic surface by applying the glutamic acid.

Though water is used as the solvent in the above example, examples of the solvent are not limited to water, and an organic solvent such as ethanol and methanol may be used. In this case, since the optical contact liquid is quickly dried, working hours for promoting drying can be shortened.

The present invention can provide a sample observation method and a microscope which can easily align the solid immersion lens to the desired position in the sample such as the electronic device as the observation object and can bring the solid immersion lens into optically-close contact with the sample securely without applying excessive pressure, and can further provide the solid immersion lens and optical contact liquid used in the method.

What is claimed is:

1. A sample observation method for observing a sample to obtain internal information, comprising:
    a lens setting step of setting a solid immersion lens on a sample in a state where optical contact liquid containing an amphipathic molecule is interposed;
    a lens contacting step of closely contacting the solid immersion lens with the sample optically by evaporating the optical contact liquid; and
    an image acquiring step of acquiring an observation image of the sample magnified by the solid immersion lens through the solid immersion lens.

2. The sample observation method according to claim 1, further comprising a separating step of wetting a position of the sample with which the solid immersion lens is brought into close contact by the optical contact liquid or a solvent of the optical contact liquid to separate the solid immersion lens from the sample after the image acquiring step.

3. The sample observation method according to claim 1, wherein the amphipathic molecule is a surfactant molecule.

4. A sample observation method for observing a sample, comprising:
    a lens setting step of setting a solid immersion lens on a sample in a state where optical contact liquid containing an amphipathic molecule is interposed;
    a lens contacting step of closely contacting the solid immersion lens with the sample optically by evaporating the optical contact liquid; and
    an image acquiring step of acquiring an observation image of the sample magnified by the solid immersion lens through the solid immersion lens.

5. The sample observation method according to claim 4, further comprising a separating step of wetting a position of the sample with which the solid immersion lens is brought into close contact by the optical contact liquid or a solvent of the optical contact liquid to separate the solid immersion lens from the sample after the image acquiring step.

6. The sample observation method according to claim 4, wherein the amphipathic molecule is a surfactant molecule.

7. A semiconductor device observation method for observing a semiconductor device, comprising:
    a lens setting step of setting a solid immersion lens on a semiconductor substrate of a semiconductor device in a state where optical contact liquid containing an amphipathic molecule is interposed;
    a lens contacting step of closely contacting the solid immersion lens with the semiconductor substrate optically by evaporating the optical contact liquid; and
    an image acquiring step of acquiring an observation image of the semiconductor device magnified by the solid immersion lens through the solid immersion lens.

8. The semiconductor device observation method according to claim 7, wherein the material of the solid immersion lens is Si or GaP.

9. The semiconductor device observation method according to claim 7, further comprising a separating step of wetting a position of the semiconductor substrate with which the solid immersion lens is brought into close contact by the optical contact liquid or a solvent of the optical contact liquid to separate the solid immersion lens from the semiconductor substrate after the image acquiring step.

10. The semiconductor device observation method according to claim 7, wherein the amphipathic molecule is a surfactant molecule.

* * * * *